United States Patent [19]

Ito

[11] 4,321,138
[45] Mar. 23, 1982

[54] METHOD AND APPARATUS FOR PREPARATIVE COUNTERCURRENT CHROMATOGRAPHY EMPLOYING A ROTATING COLUMN ASSEMBLY

[75] Inventor: Yoichiro Ito, Bethesda, Md.

[73] Assignee: The United States of America as represented by the Department of Health and Human Services, Washington, D.C.

[21] Appl. No.: 230,498

[22] Filed: Feb. 2, 1981

[51] Int. Cl.³ .............................................. B01D 15/08
[52] U.S. Cl. .................................. 210/198.2; 210/657
[58] Field of Search ...................... 210/198.2, 635, 657

[56] References Cited

U.S. PATENT DOCUMENTS

| | | | |
|---|---|---|---|
| 4,051,025 | 9/1977 | Ito | 210/198.2 |
| 4,058,460 | 11/1977 | Ito | 210/198.2 |
| 4,287,061 | 9/1981 | Sutherland | 210/198.2 |

Primary Examiner—John Adee
Attorney, Agent, or Firm—Browdy and Neimark

[57] ABSTRACT

A flow-through liquid chromatography system wherein a motor directly drives a rotary frame rotatably and coaxially carrying a column assembly consisting of chromatography column segments annularly arranged around the rotational axis, which are serially connected. A countershaft journalled on the frame has a gearing arrangement which drivingly couples the column assembly to a fixed sun gear on the frame via a planetary gear on the column assembly and which is arranged to cause the column assembly to rotate twice as fast as the frame, in the same direction, and around the same axis, the arrangement being such as to avoid the need for rotating seals for the flow tubes. The column assembly is dynamically balanced so that there is also no need for counterweights.

12 Claims, 6 Drawing Figures

METHOD AND APPARATUS FOR PREPARATIVE COUNTERCURRENT CHROMATOGRAPHY EMPLOYING A ROTATING COLUMN ASSEMBLY

FIELD OF THE INVENTION

This invention relates to systems for performing preparative countercurrent chromatography, and more particularly to a system for continuous flow-through countercurrent chromatography of the type employing horizontal coiled helical tubular, or similar, arrays rotating on individual horizontal longitudinal axes and simultaneously relating around a common central horizontal longitudinal axis.

BACKGROUND OF THE INVENTION

Various designs of apparatus for countercurrent chromatography have been previously proposed. One such earlier design, disclosed in U.S. Pat. No. 4,051,025, to Y. Ito, used a slowly rotating coiled tube to perform preparative-scale countercurrent extraction with two-phase solvent systems. Another earlier system, shown in U.S. Pat. No. 4,058,460, to Y. Ito, employs a horizontal flow-through centrifuge which is capable of performing a similar partitioning process by slowly rotating the coiled column in the gravitational field.

The system disclosed in U.S. Pat. No. 4,051,025 employs a pair of rotating seals, which often produce complications such as leakage of the solvents and contamination by air bubbles, thereby limiting the capability of the apparatus. Although the system of U.S. Pat. No. 4,058,460 eliminates the use of rotating seals, it subjects the coiled column to an uneven centrifugal force field, which tends to interface with the efficient mixing of the two phases; also, in this second system, when multiple large-bore coiled columns are to be mounted, this necessitates a large amount of space because the apparatus must employ a large counterweight mounted on one side of the rotary frame for providing the required dynamic balance for the apparatus.

There is a definite need for overcoming the disadvantages of the previously used systems.

SUMMARY OF THE INVENTION

The apparatus of the present invention is similar to those above described in that it uses a slowly rotating horizontal flow-through column to perform preparative-scale countercurrent extraction with two-phase solvent systems, the column slowly rotating in the gravitational field. The apparatus of the present invention completely eliminates the use of rotating seals and also avoids the use of a counterweight, since it is inherently dynamically balanced; it accommodates a large column array compactly at the center of the apparatus and provides a uniform acceleration field for each column unit.

Accordingly, a main object of the invention is to provide an improved flow-through countercurrent chromatography apparatus which overcomes the disadvantages and deficiencies of the previously employed flow-through countercurrent chromatography systems.

A further object of the invention is to provide an improved horizontal flow-through countercurrent chromatography apparatus for performing countercurrent extraction with two-phase solvent systems which does not require the use of rotating seals and which thereby avoids leakage of the solvents and contamination by air bubbles.

A still further object of the invention is to provide an improved horizontal flow-through countercurrent extraction apparatus for use with two-phase solvent systems which is dynamically balanced and provides efficient mixing of the two phases by generating even centrifugal forces, which is compact in size, and which applies even acceleration fields to each column unit.

A still further object of the invention is to provide an improved horizontal flow-through countercurrent extraction apparatus for use with two-phase solvent systems which accommodates a relatively large bulky column assembly compactly at the center of the apparatus, which is dynamically balanced without requiring the use of counterweights, and which provides efficient mixing of the two phases.

BRIEF DESCRIPTION OF THE DRAWINGS

Further objects and advantages of the invention will become apparent from the following description and claims, and from the accompanying drawings, wherein:

DESCRIPTION OF PREFERRED EMBODIMENTS

Figure 1:
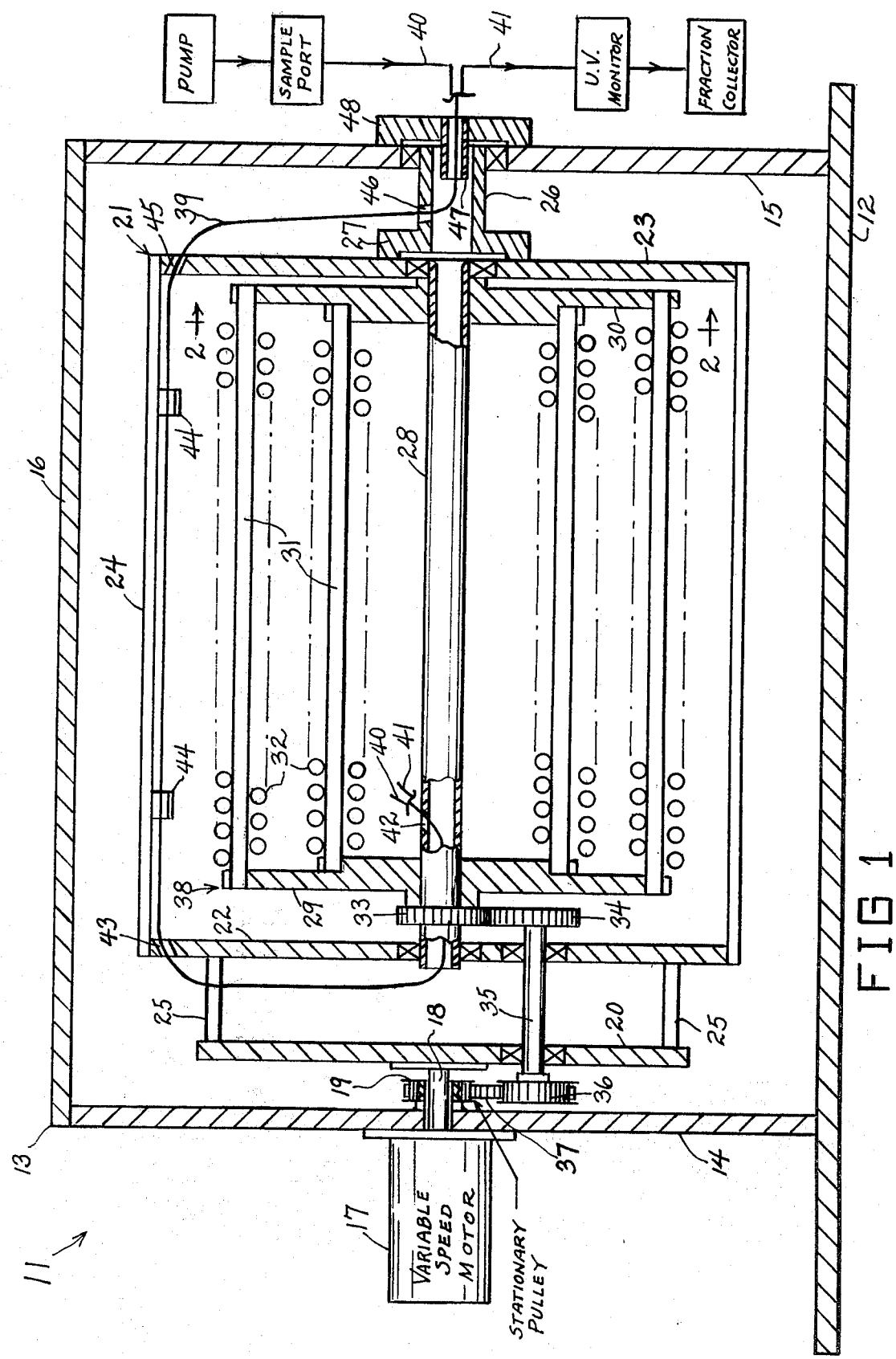
FIG. 1 is a vertical longitudinal cross-sectional view taken axially through an improved horizontal flow-through countercurrent chromatography apparatus constructed in accordance with the present invention.

A typical embodiment of the present invention employs a coiled tube which slowly rotates around its horizontal axis with respect to the gravitational field. Particles instroduced into such a coil move toward one end of the coil. This end is defined as the "head" end, and the other end is defined as the "tail" end of the coil. A two-phase solvent system confined in this rotating coil distributes itself in such a way that nearly equal volumes of the two phases occupy each helical turn, while any excess of either phase remains at the tail. This hydrodynamic behavior of the solvents allows elution of either phase through the head, while retaining a large amount of the stationary phase in each turn of the coil. Consequently, solutes introduced through the head of the coil are subjected to an efficient partition process between the mobile and stationary phases in each turn of the coil and are eluted through the tail in the order of their partition coefficients as in liquid chromatography but in the absence of solid supports.

Applications of this scheme requires a flow-through mechanism to elute the solvent through the rotating coil. The simple rotary coil assembly herein described is provided with a flow-through system which is free of rotary seals, which eliminates various undesirable complications, such as leakage, corrosion and contamination caused by the used of rotating seals.

Referring to the drawings, 11 generally designates a countercurrent chromatography apparatus according to the present invention. The apparatus 11 comprises a base 12 on which is rigidly mounted a housing 13 having opposite vertical end walls 14 and 15 and a top wall 16. Rigidly mounted on end wall 14 is a horizontal motor 17 having a shaft 18 which extends rotatably through a stationary toothed pulley 19 rigidly secured to end wall 14. Shaft 18 is drivingly secured to a rotary wing structure 20 forming part of a rotary frame 21. Said rotary frame 21 comprises opposite main rotary wing structures 22 and 23 rigidly connected at their outer end portions by a plurality of longitudinal frame bars 24, and the rotary wing structure 20, rigidly connected to wing structure 22 by a plurality of short longitudinal link bars 25.

Rotatably mounted in suitable bearings in end wall 15 in axial alignment with motor shaft 18 is a short coupling pipe 26 having an inner flange 27 rigidly secured to the midportion of wing structure 23. A tubular central shaft 28, axially aligned with motor shaft 18 and coupling pipe 26, is journalled by suitable bearings in the opposite rotary wing structures 22 and 23. Rigidly secured on central shaft 28 are opposite column-supporting spider members 29 and 30 formed with means presently to be described for the reception and securement of the ends of inner and outer tubular column supports 31 carrying helically-wound coiled separation columns 32.

Rigidly mounted on tubular shaft 28 adjacent wing structure 22 is a gear 33 which is in mesh with an identical gear 34 which is rigidly mounted on one end of a countershaft 35 journalled by suitable bearings in wing structures 20 and 22. Rigidly mounted on the other end of countershaft 35 is a toothed pulley 36 aligned with and identical to stationary toothed pulley 19, and drivingly coupled thereto by a toothed belt 37. This pulley-gear arrangement causes the column holder, shown generally at 38, comprising members 29, 30, 31, to rotate at twice the speed of the rotary frame 21 in the same direction, and to prevent the flow-through tubes, shown generally at 39, from twisting. The flow tubes comprise an inlet tube 40 and an outlet tube 41, respectively connected to the ends of the serially-connected, helically wound, coiled separation column tubes 32.

The flow tubes 39 extend from the coiled column through an aperture 42 in shaft 28, through the left end portion of said shaft, as viewed in FIG. 1, through an aperture 43 in the outer portion of wing structure 22, through aligned spaced supporting clips 44 carried by a frame bar 24, through an aperture 45 in the outer portion of wing structure 23, through an aperture 46 in coupling pipe 26, and through a stationary support tube 47 axially aligned with shaft 28 and rigidly secured to an end cap 48, which is in turn rigidly secured to end wall 15.

Figure 2:
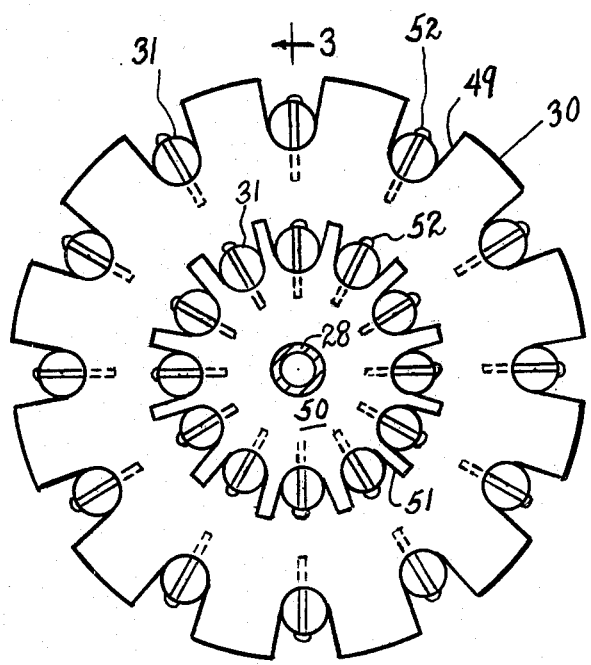
FIG. 2 is a transverse vertical cross-sectional view taken substantially on line 2—2 of FIG. 1.
Figure 3:
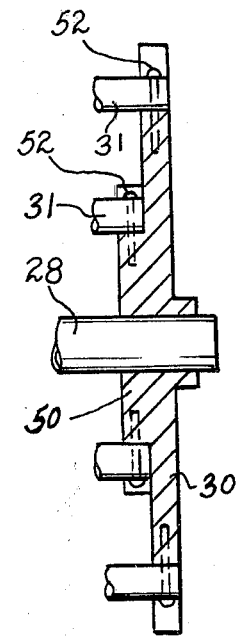
FIG. 3 is a transverse vertical cross-sectional view taken substantially on line 3—3 of FIG. 2.
Figure 4:
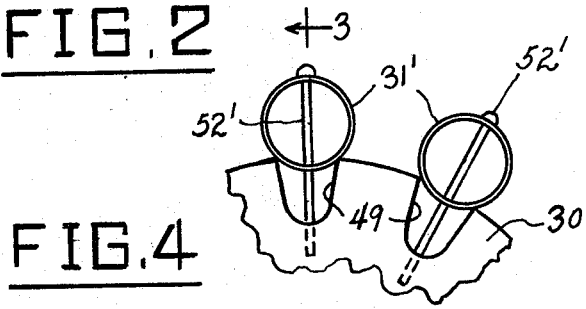
FIG. 4 is a fragmentary elevational view of a peripheral portion of an end supporting spider member in the apparatus of FIGS. 1 to 3, illustrating how relatively large-diameter coiled column cores may be secured to the column-supporting spider members of the assembly.

The column holder total assembly consists of the central shaft 28, the pair of column supports 29, 30, the tubular core members 31, and the multiple coiled columns 32 arranged in respective inner and outer annular configurations between the spider-like support members 29, 30. The column supports 29, 30 (see FIGS. 2 and 3) consist of gear-shaped discs formed with outwardly divergent peripheral notches 49 and with thickened circular inner portions 50 formed with outwardly divergent peripheral recesses 51, shaped to accommodate the ends of the tubular core members 31, which are secured therein by fastening screws 52, as shown in FIGS. 2 and 3. Thus, the coiled columns 32 are mounted in respective inner and outer annular arrays. The outward divergency of the notches 49 and recesses 51 allow the mounting of various-sized column cores 31 by means of fastening screws. For example, in FIGS. 2 and 3, the cores 31 are relatively small in diameter and are substantially completely receivable in the notches 49 and recesses 50. In FIG. 4, the cores, shown at 31', are of relatively large diameter and are secured rigidly against the outer corners of the notches 49 (and recesses 50) by longer radial fastening screws 52'.

The separation column 32 may be made of any suitable rigid material, such as glass, metal, or the like, or of semi-rigid material, such as plastic, and is in the form of tubing coiled around a rigid core 31. Multiple coiled columns can be connected in series to obtain the desired capacity of the column necessary for separation. As above mentioned, the flow tubes, shown at 39, first exit the column header assembly through the hole 42 of central shaft 28, and then reach the periphery of the leftward rotary wing structure 22 in FIG. 1, and then pass through the holes 43 and 45 of the rotary wings. They finally reach the stationary tubular support 47 via the side hole 46 in coupling pipe 26. Between the rotary wings the flow tubes 39 are loosely supported in place by the spaced tube holders 44 to prevent contact with the column holding assembly 38.

Motor 17 is of the variable speed type, so that the rotational speed of the apparatus can be regulated up to several hundred rpm. Where fragile glass tubing is used for the column coils 32, this may limit the applicable revolutional speed down to about 100 rpm. A metering pump is used to pump the solvents, and a conventional U.V. detector equipped with a flow cell is used to monitor the absorbance of the eluate, while a conventional fraction collector is employed to collect fractions.

In each operation, the column is filled with one phase (stationary phase) of an equilibrated two-phase solvent system, followed by sample injection through a sample port located on the flow line between the pump and the inlet of the column. Then the coil assembly is rotated at a desired rotational speed while the mobile phase is pumped into the column at an optimum flow rate. This produces efficient partitioning processing of samples between the retained stationary phase and the flowing mobile phase. Separated samples eluted through the outlet of the column are continuously monitored with the conventional U.V. monitor and fractionated into test tubes by means of the fraction collector.

Figure 6:
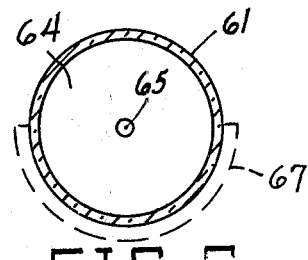
FIG. 6 is a transverse vertical cross-sectional view taken substantially on line 6—6 of FIG. 5.
Figure 5:
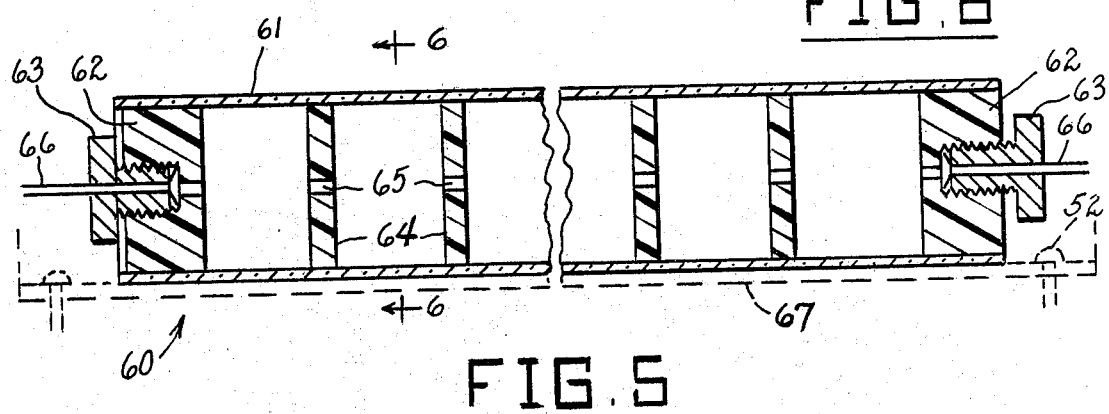
FIG. 5 is an enlarged fragmentary longitudinal vertical cross-sectional view taken axially through a multi-segmented column element which may be substituted for a coiled column element in the embodiment of FIGS. 1 to 3.

With the use of coiled columns, the column capacity can be increased by employing larger-diameter coiled columns. However, this necessitates the use of larger-diameter cores 31', as in the arrangement shown in FIG. 4, which occupies a substantially increased amount of space. Reduction of the overall column diameter for a large-scale preparative separation can be achieved by the use of multisegmented tubular column elements without loss of partition efficiency. FIGS. 5 and 6 shown an example of such a multisegmented column element which can be substituted for a coiled column element. The multisegmented column element is designated generally at 60 and comprises an elongated tubular housing 61, made of glass, metal or plastic pipe, provided with end walls 62, 62, which are in turn provided with respective flow tube connection assemblies 63, 63. The housing 61 has uniformly spaced partition discs 64 sealingly secured therein, said discs having small central apertures 65. The discs 64 are made from suitable inert material, such as PTFE, polypropylene, or the like. The opposite flow tube connection segments are shown respectively at 66, 66, and are communicatively connected to the opposite ends of the housing 61 by screw-clamping connectors 63, 63. The column element 60 is suitably secured in an elongated concave rigid support 67, shown in dotted view in FIGS. 5 and 6, such as a metal pipe cut in half lengthwise, adapted to be fastened to the notched and recessed spider members 29, 30 in substantially the same manner as the core members 31, 31' of FIGS. 2 and 4, namely, by means of screws 52 or 52'. Tube 61 may be secured in the support 67 by means of tape wrapped around the nesting parts at several spaced locations along the housing.

The use of the multisegmented columns 60 necessitates a minor modification of the apparatus. In order to fill the entire space in the column with a solvent, the column should be placed in an upright position so that the solvent introduced through the bottom end of the column can entirely displace the air in each segment. During the separation, the column should be oriented at an optimum inclination to the horizontal to retain the optimum amount of the stationary phase (near 50% of the space) and efficiently mix each phase to reduce the mass transfer resistance. This optimum angle of inclination was found to be approximately 30° from the horizontal plane. Because of the above requirements, the apparatus may be equipped with angle adjustment means, such as that disclosed in U.S. Pat. No. 4,051,025 to Y. Ito, so that the column holder assembly can be placed in at least three different positions, namely, vertical (90°), inclined (for example, 30° to the horizontal), and 0° (horizontal).

Separation procedure with the multisegmented column may be carried out as follows: The empty column is first filled with the stationary phase by introducing the solvent through the bottom of the column, which is kept in the upright position. After the column is filled with the stationary phase it is positioned at 30° to the horizontal plane and the sample solution is introduced into the column through the sample port. Then the mobile phase is pumped into the column while the column assembly is rotated at the optimum rate. As with the use of the coiled separation column, either the upper or lower phase may be used as the mobile phase. However, with the multisegmented column, both sample solution and the mobile phase should be introduced through the lower end of the column when the mobile phase is the upper phase and through the upper end of the column when the mobile phase is the lower phase. In this way, a greater amount of the stationary phase is retained in the column and a better resolution is obtained. The eluate flowing through the outlet of the column is continuously monitored with the U.V. detector and fractionated, as with the use of the coiled column.

In a typical actual embodiment of the apparatus 11, the rotary frame 21 consisted of three aluminum arms 20, 22 and 23, rigidly bridged together with link bars 25, 24, and rotatably carrying the two rotary elements 29, 30, the countershaft 35 and the centrally located column holder assembly. The countershaft 35 was provided with a toothed pulley 36 at one end and a plastic gear 34 at the other end. The pulley 36 was coupled by a toothed belt 37 to an identical stationary pulley 19, as above mentioned, mounted on the stationary wall member 14. This coupling generated a counter-rotation of the countershaft 35 on the rotary frame 21. This motion was further conveyed to the central column holder assembly 38 by 1:1 gear coupling provided by the gears 34, 33. Consequently, the column holder assembly 38 rotated around its own axis at a rate twice that of the rotary frame and in the same direction.

Separation columns in the typical design consisted of coiled glass tubes of 0.5 cm inside diameter, with different helical diameters. One column had a 2.5 cm helical diameter, with a 90 ml capacity, and the other had a 1.25 cm helical diameter, with a 45 ml capacity. Both columns contained approximately 50 helical turns. Each column was supported by a hollow aluminum core of the appropriate diameter, which in turn was fastened onto the column holder, as above described, by a fastening screw at each end. The column holder was designed with notches and recesses for mounting the column at two different radial distances from the central axis of the apparatus, the radial distance for the inner group of columns being 6.5 cm and the radial distance for the outer group of columns being 13 cm. A maximum number of 30 columns could be mounted on the holder, 10 columns at the 6.5 cm radial distance and 20 columns at the 13 cm radial distance. The selected number of columns were connected in series with short lengths of heat-shrinkable PTFE tubing at each junction.

The flow tubes 40, 41 were installed in the manner previously described, and illustrated in FIG. 1. These tubes were lubricated with silicone grease and were surrounded by a length of plastic tubing to prevent rubbing contact with metal parts.

A Beckman Accu Pump and Chromatronix Pump were used to elute the solvents, and an LKB Uvicord III apparatus was used to monitor the eluate.

While certain specific embodiments of an improved countercurrent chromatography apparatus have been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. An apparatus for continuous countercurrent chromatography comprising a support, frame means journalled to said support, motor means drivingly connected to said frame means, a chromatography column assembly rotatably mounted in said frame means for rotation around the same axis of rotation as that of the frame means, said column assembly having inlet and outlet flow tube means supportingly carried by the frame means and extending from the support substantially coaxially with said common axis of rotation, and means gearingly coupling said column assembly to said support so as to drive the column assembly at a rotational speed twice that of the frame means and in the same direction relative to said support, whereby to avoid twisting of said flow tube means, said column assembly comprising a plurality of interconnected chromatography column segments mounted on the column assembly so as to be substantially dynamically balanced with respect to said common rotational axis.

2. The chromatography apparatus of claim 1, and wherein said coupling means includes a countershaft journalled in said frame means in spaced parallel relationship to said common rotational axis, means drivingly coupling one portion of said countershaft to said support in planetary relation relative to said common rotational axis, and means gearingly coupling another portion of said countershaft to said column assembly.

3. The chromatography apparatus of claim 2, and wherein said one portion of the countershaft has a first toothed pulley and said support has an identical fixed toothed pulley coaxial with said common rotational axis, and wherein said coupling means includes a toothed belt drivingly engaged on said toothed pulleys.

4. The chromatography apparatus of claim 1, and wherein said column assembly comprises a plurality of serially connected chromatography column segments annularly arranged around said common axis of rotation.

5. The chromatography apparatus of claim 1, and wherein said column assembly comprises supporting shaft means, a pair of spaced opposed spider members mounted on said shaft means, said spider members being formed with means to receive the opposite ends of the chromatography column segments, and means to fasten said opposite ends to the spider members.

6. The chromatography apparatus of claim 5, and wherein the column segments comprise elongated supporting core elements and helically-wound separation tubes mounted on said core elements.

7. The chromatography apparatus of claim 5, and wherein said spider members are formed with outwardly divergent notches shaped to at least partially receive the opposite ends of the chromatography segments, the notches being at the same radial distance from said common rotational axis.

8. The chromatography apparatus of claim 5, and wherein said spider members are formed with outwardly divergent peripheral notches shaped to at least partially receive the opposite ends of a first array of chromatography column segments, and are formed with outwardly divergent recesses at a shorter radial distance from said common rotational axis shaped to at least partially receive the opposite ends of a second array of chromatography segments.

9. The chromatography apparatus of claim 1, and wherein said column assembly comprises a plurality of interconnected column segments in the form of helically-wound separation tubes.

10. The chromatography apparatus of claim 1, and wherein said column assembly comprises a plurality of interconnected column segments in the form of multi-segmented column segments, each comprising a tubular housing with a plurality of spaced internal partition walls formed with small central apertures.

11. The chromatography apparatus of claim 1, and wherein said chromatography column assembly comprises a plurality of evenly spaced column segments mounted in an annular array around said common rotational axis.

12. The chromatography apparatus of claim 1, and wherein said chromatography column assembly comprises a plurality of evenly spaced outer column segments defining an outer annular array around said common rotational axis, and a plurality of inner evenly spaced column segments defining an inner annular array coaxial with said outer annular array.

* * * * *